Figure 1A:
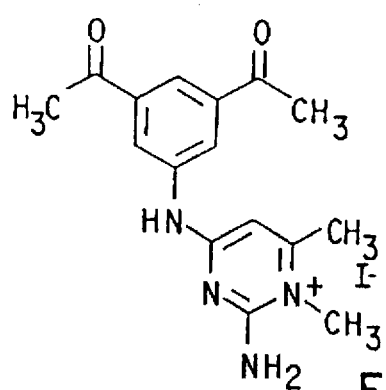

United States Patent [19]

Bukrinsky et al.

[11] Patent Number: 5,733,932

[45] Date of Patent: Mar. 31, 1998

[54] COMPOUNDS AND METHODS OF USE TO DERIVATIZE NEIGHBORING LYSINE RESIDUES IN PROTEINS UNDER PHYSIOLOGICAL CONDITIONS

[75] Inventors: Michael I. Bukrinsky, Glenwood Landing; Anthony Cerami, Shelter Island, both of N.Y.; Peter Ulrich, Old Tappan, N.J.

[73] Assignee: The Picower Institute for Medical Research, Manhaset, N.Y.

[21] Appl. No.: 463,405

[22] Filed: Jun. 5, 1995

Related U.S. Application Data

[63] Continuation-in-part of Ser. No. 369,830, Jan. 6, 1995, Pat. No. 5,574,040.

[51] Int. Cl.$^6$ ...................... A61K 31/155; C07C 279/18
[52] U.S. Cl. ...................... 514/634; 514/635; 564/234; 564/238
[58] Field of Search ...................... 564/234, 238; 514/634, 635

[56] References Cited

U.S. PATENT DOCUMENTS

| | | | |
|---|---|---|---|
| 4,051,256 | 9/1977 | Swallow | 424/304 |
| 4,705,790 | 11/1987 | Hubele et al. | 514/269 |
| 4,782,062 | 11/1988 | Tolman et al. | 514/262 |
| 4,814,338 | 3/1989 | Ito et al. | 514/275 |
| 4,879,296 | 11/1989 | Daluge et al. | 514/263 |
| 4,975,530 | 12/1990 | Tzikas et al. | 544/296 |
| 4,988,704 | 1/1991 | Ito et al. | 514/275 |
| 5,093,525 | 3/1992 | Weber et al. | 564/238 |
| 5,118,339 | 6/1992 | Tamura et al. | 544/229 |

FOREIGN PATENT DOCUMENTS

41 20 247  12/1992  Germany .

OTHER PUBLICATIONS

Adam et al., 1989, "Identification of specific binding proteins for a nuclear location sequence", *Nature* 337: 276–279.
Brinchmann et al., 1991, "Few Infected CD4+ T Cells but a High Proportion of Replication–Competent Provirus Copies in Asymptomatic Human Immunodeficiency Virus Type 1 Infection", *J. Virol.* 65: 2019.
Brown et al., 1987, "Correct Integration of Retroviral DNA in Vitro" *Cell* 49: 347.
Bukrinsky et al., 1991, "Quiescent T Lymphocytes as an Inducible Virus Reservoir in HIV–1 Infection", *Science* 254: 423–427.
Bukrinsky et al., 1993, "A Nuclear Localization Signal within HIV–1 matrix protein that governs infection of non–dividing cells", *Nature* 365: 666–669.
Bukrinsky et al., 1992, "Active nuclear import of human immunodeficiency virus type 1 preintegration complexes", *Proc. Natl. Acad. Sci.* 89: 6580–6584.
Chapel et al., 1992, "Differential Human Immunodeficiency Virus Expression in CD4+ Cloned Lymphocytes: from Viral Latency to Replication", *J. Virol.* 66: 3966.

Cuomo, 1994, "Rch1, a protein that specifically interacts with the RAG–1 recombination–activating protein", *Proc. Natl. Acad. Sci.* 91: 6156.
Dabauville, 1988, "Inhibition of Nuclear Accumulation of Karyophilic Proteins in Living Cells by Microinjection of the Lectin Wheat Germ Agglutinin", *Exp. Cell Res.* 174: 291–296.
Dingwall et al., 1988, "The Nucleoplasmin Nuclear Location Sequence is Larger and More Complex than that of SV–40 Large T Antigen", *J. Cell Biol.* 107:841–849.
Emerman et al., 1994, "Scientific Correspondence", *Nature* 369: 108.
Fauci et al., 1991, "Immunopathogenic Mechanisms in Human Immunodeficiency Virus (HIV) Infection", *Ann. Int. Med.* 114: 678.
Forbes, 1992, "Structure and Function of the Nuclear Pore Complex", *Ann. Rev. Cell Biol.* 8: 495–527.
Goldfarb et al., 1986, "Synthetic peptides as nuclear localization signals", *Nature* 332:641–644.
Gorlich, 1994 "Isolation of a Protein Is Essential for the First Step of Nuclear Protein Import", *Cell* 79: 767.
Guilian et al., 1990, "Secretion of Neurotoxins by Mononuclear Phagocytes Infected with HIV–1", *Science* 250: 1593.
Gulizia et al., 1994, "Reduced Nuclear Import of Human Immunodeficiency Virus Type 1 Preintegration Complexes in the Presence of a Prototypic Nuclear Targeting Signal", *J. Virol.* 68: 2021–2025.
Heinzinger et al., 1994, "The Vpr protein of human immunodeficiency virus type 1 influences nuclear localization of viral nucleic acids in nondividing host cells", *Proc. Natl. Acad. Sci.* 91: 7311.

(List continued on next page.)

*Primary Examiner*—Yogendra N. Gupta

[57] ABSTRACT

The present invention encompasses the use of the compounds of formula as given below to detect certain specific protein structures which are present in nuclear localization sequences

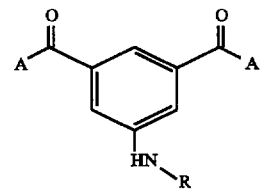

wherein A is, independently CH$_3$ or CH$_2$CH$_3$ and R is

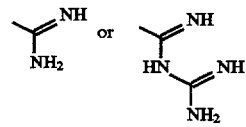

and salts thereof.

and salts thereof.

4 Claims, 5 Drawing Sheets

OTHER PUBLICATIONS

Humphries and Temin, 1974, "Requirement for Cell division for Initiation of Transcription of Rous Sarcoma Virus RNA", *J. Virol.* 14: 531–546.

Hurt, 1993, "The Nuclear Pore Complex", *FEBS Letters* 325: 76–80.

Kalderon et al., 1984, "A Short Amino Acid Sequence Able to Specify Nuclear Location", *Cell* 39:499–509.

Koenig et al., 1986, "Detection of AIDS Virus in Macrophages in Brain Tissue from AIDS Patients with Encephalopathy", *Science* 233: 1089.

Lanford, 1986, "Induction of Nuclear Transport with a Synthetic Peptide Homologous to the SV40 T Antigen Transport Signal", *Cell* 46: 575.

Melchoir, 1993, "Inhibition of Nuclear Protein Import by Nonhydrolyzable of GTP and Identification of the Small GTPase Ran/TC4 as an Essential Transport Factor", *J. Cell Biol.* 123: 1649.

Miller et al., 1994, "The Human Immunodeficiency Virus–1 nef Gene Product: A Positive Factor For Viral Infection and Replication in Primary Lymphocytes and Macrophages", *J. Exp. Med.* 179: 101–113.

Pantaleo et al., 1993, "HIV Infection is active and progressive in lymphoid tissue during the clinically latent stage of disease" *Nature* 362: 355–358.

Pante et al., 1993, "The Nuclear Pore Complex", *J. Cell. Biol.* 122: 977–984.

Price et al., 1988, "The Brain in AIDS: Central Nervous System HIV–1 Infection and AIDS Dementia Complex", *Science* 239: 586–592.

Robbins et al., 1991, "Two Interdependent Basic Domains in Nucleoplasmin Nuclear Targeting Sequence: Identification of a Class of Bipartite Nuclear Targeting Sequence", *Cell* 64: 615–623.

Schnittman, 1989, "The Reservoir for HIV–1 In Human Peripheral Blood Is a T Cell That Maintains Expression of CD4", *Science* 245: 305.

Spina et al., 1994, "The Importance of nef in the Indication of Human Immunodeficiency Virus Type 1 Replication from Primary Quiescent CD4 Lymphocytes", *J. Exp. Med.* 179: 115–123.

Sterne–Marr et al., "O–linked Glycoproteins of the Nuclear Pore Complex Interact with a Cytosolic Factor Required for Nuclear Protein Import", 1992, *J. Cell Biol.* 116: 271.

Stevenson et al., 1990, "HIV–1 replication is controlled at the level of T cell activation and proviral integration", *EMBO J.* 9: 1551–1560.

Stochaj et al., 1992, "Nucleocytoplasmic traffic of proteins", *Eur. J. Cell Biol.* 59: 1–11.

Von Schwedler et al., 1994, "The nuclear localization signal of the matrix protein of human immunodeficiency virus type 1 allows the establishment of infection in macrophages and quiescent T lymphocytes", *Proc. Natl. Acad. Sci.* 91: 6992–6996.

Weinberg, 1991, "Productive Human Immunodeficiency Virus Type 1 (HIV–1) Infection of Nonproliferating Human Monacytes", *J. Exp. Med.* 172: 1477–1482.

Weiss, 1993, "How Does HIV Cause AIDS", *Science* 260: 1273.

Wiley et al., 1986, "Cellular localization of human immunodeficiency virus infection within the brains of acquired immune deficiency syndrome patients", *Proc. Natl. Acad. Sci.* 83: 7089–93.

Yano et al., 1992, "Cloning and Characterization of SRP1, a Suppressor of Temperature–Sensitive RNA Polymerase I Mutations, in *Saccharomyces cerevisiae*", *Mol. Cell. Biol.* 12: 5640.

Yeh, 1990, "The Arginine–Rich Domain of Hepatitis B Virus Precore and Core Proteins Contain a Signal For Nuclear Transport", *Journal of Virology* 64: 6141–6147.

Zack, 1990, "HIV–1 Entry into Quiescent Primary Lymphocytes: Molecular Analysis Reveals a Labile, Latent Viral Structure", *Cell* 61: 213–222.

Zack et al., 1992, "Incompletely Reverse–Transcribed Human Immunodeficiency Virus Type 1 Genomes in Quiescent Cells Can Function as Intermediates in the Retroviral Life Cycle", *J. Virol.* 66: 1717–1725.

Zacksenhaus et al., 1993, "A Bipartite Nuclear Localization Signal in the Retinoblastoma Gene Product and Its Importance for Biological Activity", *Mol. Cell Biol.* 13: 4588.

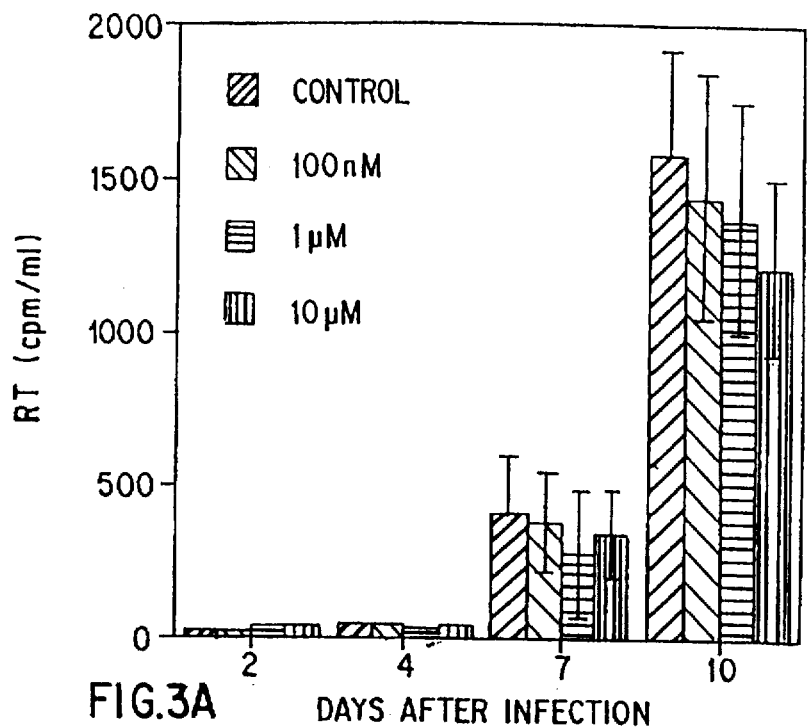
FIG.3A DAYS AFTER INFECTION
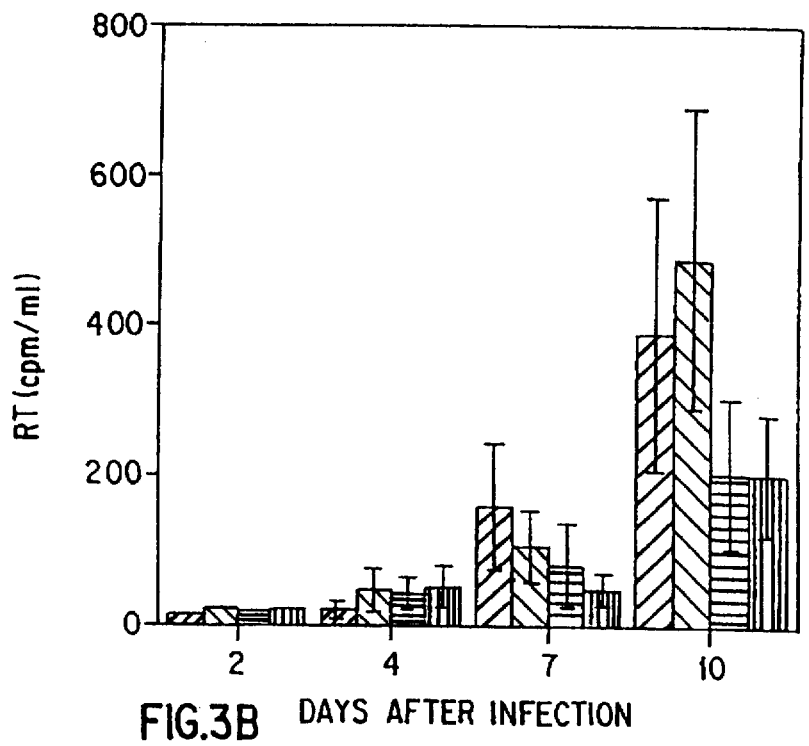
FIG.3B DAYS AFTER INFECTION

COMPOUNDS AND METHODS OF USE TO DERIVATIZE NEIGHBORING LYSINE RESIDUES IN PROTEINS UNDER PHYSIOLOGICAL CONDITIONS

This application is a continuation-in-part of application Ser. No. 08/369,830, filed Jan. 6, 1995, now U.S. Pat. No. 5,574,040 which is hereby incorporated by reference in its entirety.

1. FIELD OF THE INVENTION

The field of the present invention concerns compounds that react with specific sequences in proteins. The present invention more particularly concerns a class of compounds that react, under physiologic conditions, with proteins having adjacent or neighboring lysines. The compounds of the invention can be used to label specifically such proteins for research purposes and to disrupt their function for pharmacologic purposes.

2. BACKGROUND TO THE INVENTION

2.1. The Derivatization of Proteins

Those skilled in the art will appreciate that there are many compounds that can react with specific amino acid residues in proteins, e.g., with sulfhydryl, amino, carboxyl moieties. These reagents are substrate specific, in the sense that each reacts only with one or a few specific amino acids wherever they occur within a protein's sequence. However, the reactivity of such reagents is not affected by the adjacent or neighboring amino acids that form the environment of the reactive moiety. Thus, the reactivity of such compounds is not context or neighborhood specific.

2.2. Nuclear Importation

The function of an intracellular protein is usually the result of the overall three dimensional (tertiary) structure of the protein. However, nuclear importation is determined by the simple presence of a short sequence, called a nuclear localization signal (NLS), which functions relatively independently of its position relative to the remainder of the structure of object that is imported. In eukaryotic cells all proteins are made in the cytoplasm, which is outside of the nucleus. In general, those proteins larger than 40 kD that are specifically localized in the nucleus of the cell must be actively imported into the nucleus through the nuclear membrane from the cytoplasm via an ATP-dependent mechanism that is independent of cell division. The proteins, and other objects, that are imported have a nuclear localization signal (NLS), usually located within the $NH_2$ terminal segment of the protein. Several such sequences are known:

a. PKKKRKV from large T antigen of SV40, Kalderon, D., et al., 1984, Cell 39:499–509;

b. [AV]KRPAATKKAGQAKKKK[LD] from nucleoplasmin, in which only one of the two bracketed sequences is required, Dingwall, C., et al., 1988, J. Cell Biol. 107:841–49;

c. PRRRRSQS from hepatitis B HbcAg-Yeh, C. T., 1990, J. Virol.

d. KRSAEGGNPPKPLKKLR from the retinoblastoma gene product p110$^{rb1}$—Zacksenhaus E. et al., 1993, Mol. Cell. Biol. 13:4588 e. KIRLPRGGKKKYKLK from the matrix protein of HIV-1, Bukrinsky, M. I., et al., 1993, Nature 365:666. Other viruses that contain NLS sequences include Herpes simplex and measles virus. The recognition of an NLS sequence is largely independent of the detailed structure of the object which includes it and of its site of attachment. Goldfarb, D. S. et al., 1986, Nature 332:641–44; Lanford, R. E., 1986, Cell 46:575. Mere juxtaposition of the amino acids of the NLS is not sufficient for function, for example NLS function is generally not conferred by the peptide having the same sequence of amino acids in the opposite order as the NLS sequence. Adam, S. A. et al., 1989, Nature 337:276–79.

The primary structure, i.e., the linear sequence, of the NLS most frequently contains consecutive lysines, the $N^\epsilon$ moieties of which presumably closely approach one another, i.e., they are neighbors. However, certain functional NLS peptides lack consecutive lysines. Robbins, J., et al., 1991, Cell 64:615–23. Presumably the secondary and tertiary structure of these so called "bipartite" NLS peptides gives rise to neighboring $N^\epsilon$ moieties, which may be important for their activity.

The cellular proteins or protein complexes that recognize and transport proteins bearing NLS sequences are incompletely understood. It appears that there are proteins of the cytoplasmic face of the nuclear membrane that recognize the NLS and, after such recognition, it is this complex that is transported through the nuclear pore complex. Review: Stochaj, U., et al., 1992, Eur. J. Cell Biol. 59:1–11; Hurt, E. C., 1993, FEBS Letters 325:76–80; Pante, N., et al., 1993, J. Cell. Biol. 122:977–84; Forbes, D. J., 1992, Ann. Rev. Cell Biol. 8:495–527.

A receptor for the NLS sequence has been recently described in a Xenopus system. Görlich, D., 1994, Cell 79:767. It is a cytoplasmic 60 kDa protein which is homologous with previously described proteins of unknown function, SRP1p of yeast, Yano, R., et al., 1992, Mol. Cell. Biol. 12:5640, and Rch1 of mammals, Cuomo C. A., 1994, Proc. Natl. Acad. Sci. 91:6156.

Two inhibitors of the nuclear localization process have been described. Nuclear localization has been inhibited by lectins (e.g., wheat germ agglutinin (WGA)) that bind to the O-linked glycoproteins associated with nuclear localization. Dabauvalle, M.-C., 1988, Exp. Cell Res. 174:291–96; Sterne-Marr R., et al., 1992, J. Cell Biol. 116:271. The nuclear localization process, which also depends upon the hydrolysis of GTP, is blocked by a non-hydrolyzable analog of GTP, e.g., ($\gamma$-S)GTP, Melchior, F., 1993, J. Cell Biol. 123:1649.

However, neither ($\gamma$-S)GTP nor WGA can be used as pharmaceuticals. Proteins, such as WGA, can be introduced into the interior of a cell only with considerable difficulty. The same limitation applies to thiotriphospates such as [$\gamma$-S]GTP. Further, GTPases are involved in a multitude of cell processes and intercellular signaling, thus, the use of a general inhibitor of GTPases would likely lead to unacceptable side effects.

2.3. The Significance of Nuclear Importation in HIV-1 Infections

Although HIV-1 is a retrovirus, it and other lentiviruses must be distinguished from viruses of the oncoretrovirus group, which are not associated with progressive fatal infection. For example, lentiviruses replicate in non-proliferating cells, e.g., terminally differentiated macrophages, Weinberg, J. B., 1991, J. Exp. Med. 172:1477–82, while oncoretroviruses, do not. Humphries, E. H., & Temin, H. M., 1974, J. Virol. 14:531–46. Secondly, lentiviruses are able to maintain themselves in a non-integrated, extrachromosomal form in resting T-cells. Stevenson, M., et al., 1990, EMBO J. 9:1551–60; Bukrinsky, M. I., et al., 1991, Science 254:423; Zack, J. L., et al., 1992, J. Virol. 66:1717–25.

However, it is unclear whether this phenomenon is related to the presence of latently infected peripheral blood lymphocytes (PBL) in HIV-1 infected subjects, wherein the virus is present in a provirus form. Schnittman, S. M., 1989, Science 245:305; Brinchmann, J. E., et al., 1991, J. Virol. 65:2019; Chapel, A., et al., 1992 J. Virol. 66:3966.

The productive infection of a cell by a retroviruses involves the steps of penetration into the cell, synthesis of a DNA genome from the RNA genetic material in the virion and insertion of the DNA genome into a chromosome of the host, thereby forming a provirus. Both lenti- and oncoretroviruses gain access to the host cell's nucleus during mitosis when the nuclear membrane dissolves. However, the lentiviruses are also able to cross the nuclear membrane because viral proteins containing nuclear localization sequences are associated with the viral nucleoprotein complex.

The productive infection of terminally differentiated macrophages located in the central nervous system is thought to be responsible for the dementia associated with AIDS. Keonig, S., et al., 1986, Science 233:1089; Wiley, C. A. et al., 1986, Proc. Natl. Acad. Sci. 83:7089–93; Price, R. W., et al., 1988, Science 239:586–92. The infection of terminally differentiated macrophages in the lymphoid system is known to cause aberrant cytokine production. Guilian, D., et al., 1990, Science 250:1593; Fauci, A. S., et al., 1991, Ann. Int. Med. 114:678. Thus, the wasting syndrome associated with HIV-1, also known as "slim" disease, is believed to be a pathological process that is independent of the loss of CD4-T-cells. Rather the pathobiology of the wasting is closely related to the pathobiology of cachexia in chronic inflammatory and malignant diseases. Weiss, R. A., 1993, Science 260:1273. For these reasons, the inhibition on HIV-1 infection of macrophages and other non-dividing cells is understood to represent a highly desired modality in the treatment of HIV-1 infection, especially for patients wherein dementia or cachexia dominate the clinical picture.

Macrophages play an important role in the transmission of HIV as well. During early stages of the infection, macrophages and cells of the macrophage lineage (i.e. dendritic cells) may be the primary reservoir of HIV-1 in the body, supporting infection of T cells by antigen presentation activities, Pantaleo, G., et al., 1993, Nature 362:355–358, as well as via the release of free virus. Direct cell-to-cell transmission of the virus may constitute the major route by which infection spreads during the early stages of the disease, after resolution of the initial viremia.

It is noteworthy, in this regard, that macrophage-tropic strains of HIV-1 predominate in the early stages of infection. Thus, it appears that the infection of macrophages is particularly important during the development of a chronic infective state of the host in a newly infected subject. Secondly, macrophages are the HIV-susceptible cell type most readily passed during sexual intercourse from an HIV-infected individual into the circulation of an uninfected individual.

Finally, infection of quiescent T cells by HIV-1 has been shown to take place in vitro, Stevenson, M., et al., 1990, EMBO J. 9:1551–1560; Zack, J. A., 1990, Cell 61:213–222, and probably constitutes an important pathway for the spread of infection in vivo at various stages of the disease. Bukrinsky, M. I., et al., 1991, Science 254:423–427. Although HIV-1 does not establish productive replication in quiescent T cells, the extrachromosomal retroviral DNA can persist in the cytoplasm of such cells for a considerable period of time, and initiate replication upon activation of the host cell. Stevenson, M., et al., 1990, EMBO J. 9:1551–1560; Spina, C. A., et al., 1994, J. Exp. Med. 179:115–123; Miller, M. D., et al., 1994, J. Exp. Med. 179:101–113. A recent report suggests that the duration of viral persistence in the quiescent T cell depends on the presence of a functional NLS. von Schwedler, U., et al., 1994, Proc. Natl. Acad. Sci. 91:6992–6996. Thus, physicians recognize the desirability of preventing the infection of macrophages by HIV and understand that substantial benefits would be obtained from the use of a pharmacologic agent that prevents HIV infection in this cell type.

The mechanism whereby HIV, but not oncoretroviruses, infect non-dividing cells is now understood in broad outline. It is established that the function of the pre-integration complex of retrovirus in this regard does not depend upon the cellular mechanisms of mitosis or DNA replication, per se. Rather the integration complex must merely gain access to nucleus. Brown, P. O., et al., 1987, Cell 49:347. Oncoretroviruses gain access to the nucleus upon the dissolution of the nuclear membrane in mitosis. By contrast, lentiviruses contain two distinct proteins that mediate nuclear access through the nuclear pore complex in the absence of cellular division. For the first of these, the matrix protein (MA or p17), nuclear importation activity is clearly due to the presence of a trilysyl-containing NLS sequence. Bukrinsky, M. I., et al., 1993, Nature 365:666; von Schwedler, U., et al., 1994, Proc. Natl. Acad. Sci. 91:6992. A second protein subserving the function of nuclear entry, the vpr protein, does not contain an identifiable NLS consensus sequence. Emerman, M., et al., 1994, Nature 369:108; Heinzinger, N. K. et al., 1994, Proc. Natl. Acad. Sci. 91:7311. Rather vpr is thought to form a complex with a cellular protein that does possess such an NLS sequence.

The significance of the NLS sequence in the importation of HIV-1 into the nucleus of non-dividing cells has been illustrated in experiments wherein the presence in the medium of a high concentration (0.1M) of the peptide having the sequence of the SV40 T-antigen NLS blocked the importation of HIV-1 into the nucleus of aphidicolin-arrested CD4+ MT4 cells. Gulizia, J., et al., 1994, J. Virol. 68:2021–25.

3. SUMMARY OF THE INVENTION

The invention involves a class of aryl alkyl carbonyl compounds, particularly, divalent aryl carbonyl moieties N-linked through the arene to a nitrogen-containing heterocyclic functionality, e.g., an acetyl or propanoyl substituted aniline moiety N-linked to a pyrimidinium, pyrimidine or triazine moiety. The invention further encompasses methods of using the compounds of the invention to form tandem Schiff bases in proteins having neighboring $N^\epsilon$ moieties of lysine residues. As used, herein, neighboring $N^\epsilon$ moieties are two $N^\epsilon$ moieties of a protein that approach each other as close as the carbonyls of the arylene bis (methyl carbonyl) compounds of the invention, when the protein is in its natured conformation. As used herein neighboring, adjacent and juxtaposed are equivalent terms in reference to $N^\epsilon$ moieties and refer to the physical locations of the $N^\epsilon$ moieties in the structure of the native protein and not to the positions of the lysines in the linear sequence.

The invention further encompasses methods of inhibiting productive infection by HIV-1 of terminally differentiated (non-dividing cells), particularly macrophages, by inhibition of the importation of the cytoplasmic HIV-1 complex into the nucleus of cell. Particularly the invention concerns the direct introduction across the cytoplasm membrane of a cell of compounds that block such importation. Thus, in one embodiment, the invention encompasses methods of using the above-described compounds to prevent productive infection of terminally differentiated macrophages and resting T-cells in HIV-1 infected subjects. Without limitation as to theory, the invention is believed to block the HIV-1 replication by the formation of tandem Schiff bases with neighboring $N^\epsilon$ moieties of viral proteins, a consequence of which is that the viral nucleoprotein complex does not pass across the nuclear membrane via interaction with the nuclear pore transport complex and/or other cellular components.

4. BRIEF DESCRIPTION OF THE FIGURES

Figure 1B:
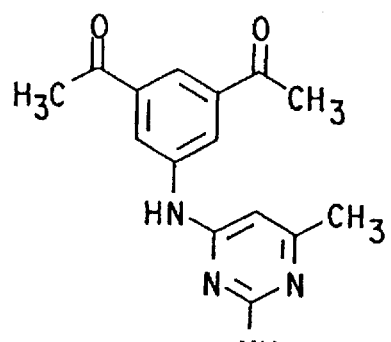
Figure 1C:
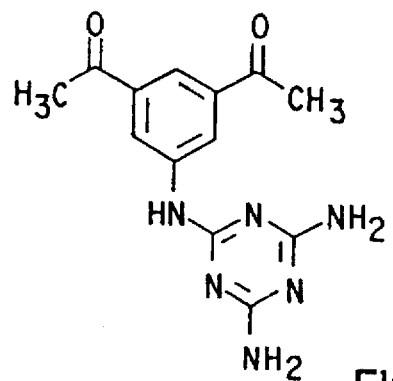

FIGS. 1A–C. The structures of exemplary Compounds No. 2, 11 and 13 are, respectively, FIGS. 1A, 1B, 1C.

Figure 2A:
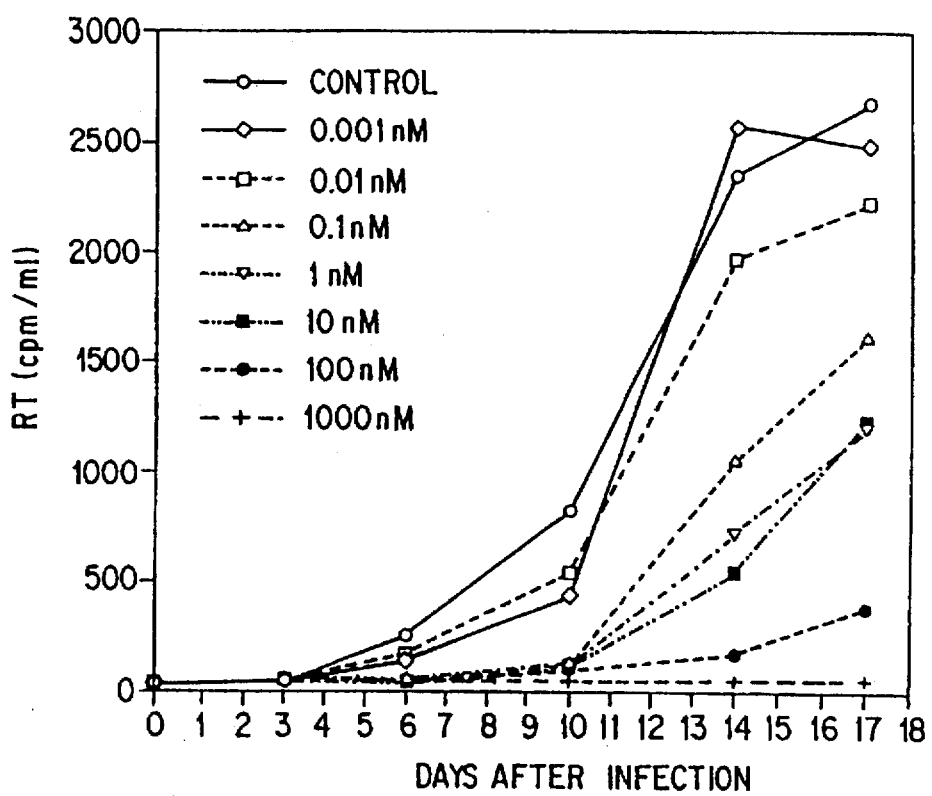
Figure 2B:
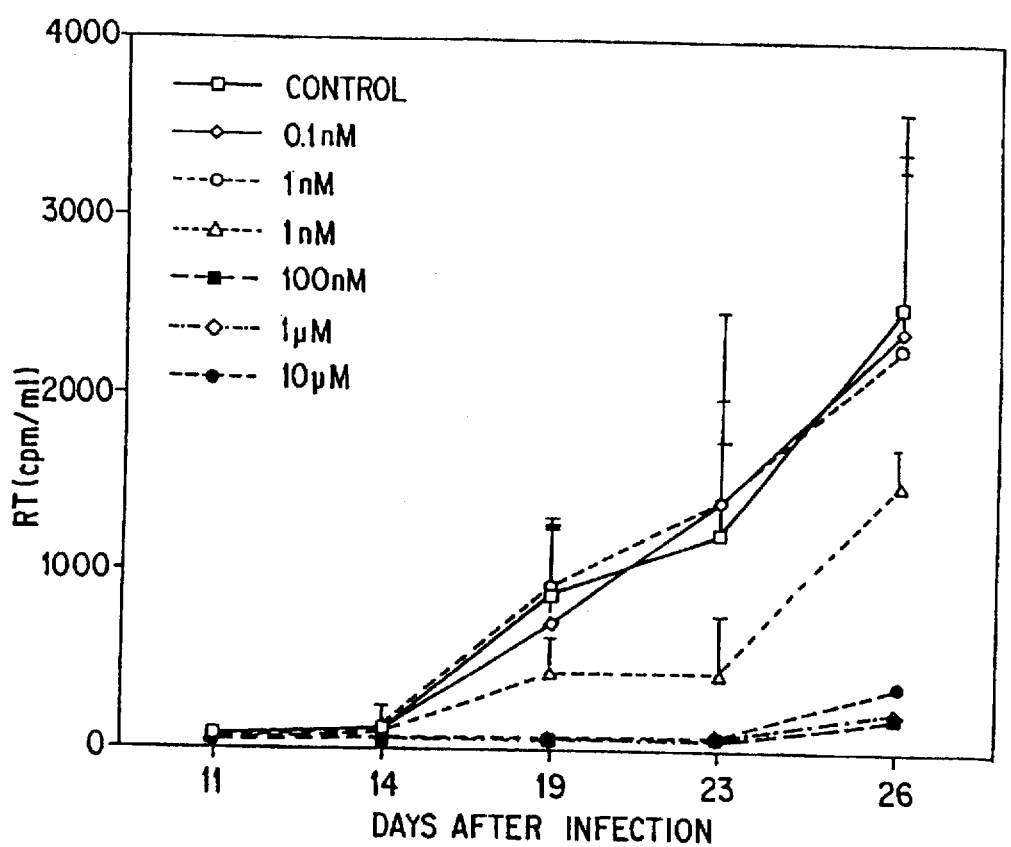
Figure 2C:
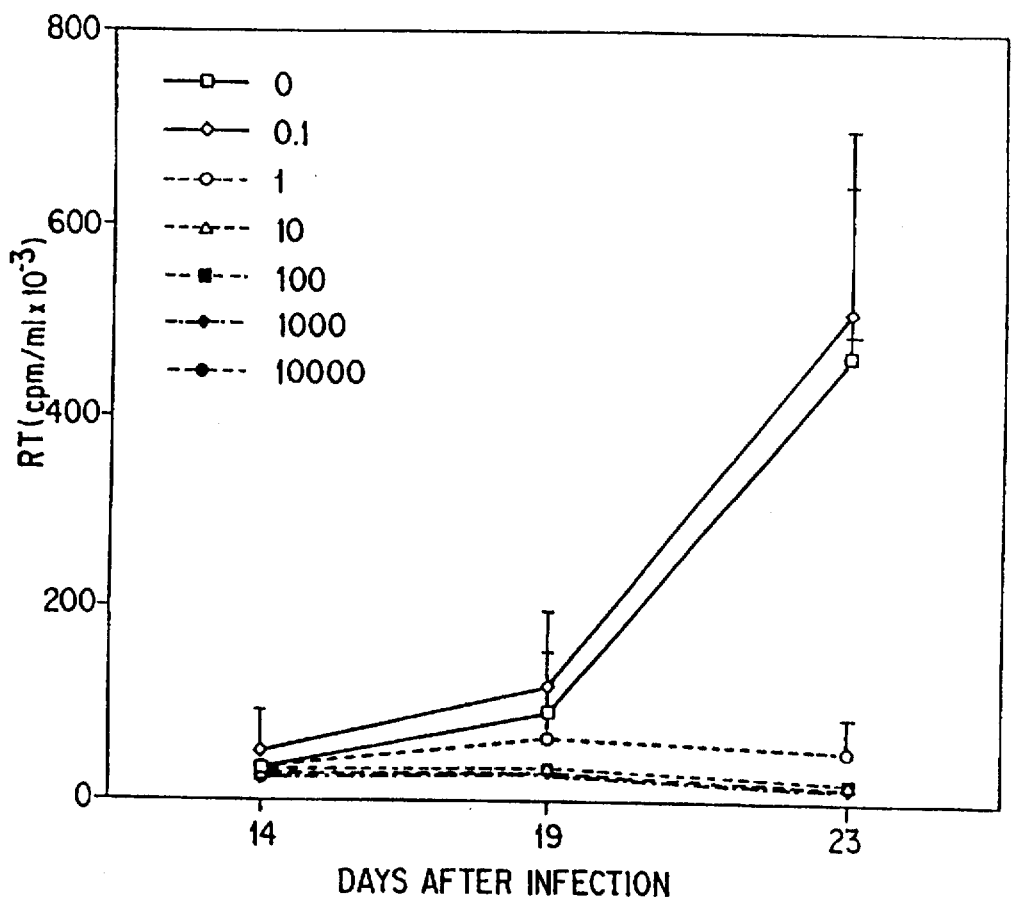

FIGS. 2A–C. The effect of various concentrations of Compound No. 2 on RT activity in the supernatant of HIV-1-infected monocytes. FIG. 2A: Multiplicity of Infection (MOI) 1 ng p24/$10^6$ monocytes, cultured in presence of M-CSF.

FIG. 2B: MOI 8 ng p24 $10^6$ monocytes, cultured in absence of M-CSF. FIG. 2C: MOI 0.8 ng p24/$10^6$ monocytes, cultured in absence of M-CSF.

FIG. 3. The effect of various concentrations of Compound No. 2 on RT activity in the supernatant of HIV-1-infected mitogen-stimulated peripheral blood leukocytes at infected at 1.0 and 1.0 ng p24/$10^6$ cells, FIG. 3A and 3B, respectively.

5. DETAILED DESCRIPTION OF THE INVENTION

5.1. The Compounds and Methods of their Synthesis

The compounds of the present invention can be synthesized by reacting a diacetyl or dipropanoyl derivative of aniline with a chloro derivative of purine, aminomethylpyrimidine, diamino-triazine, or with a cyanoguanidine. The reaction can be performed at 90°–100° C. in an aqueous solvent in the presence of a mineral acid to yield the corresponding aminophenyl pyridine or triazine. The pyrimidinium can be synthesized from the pyrimidine by reaction with an excess methyl iodide at 40°–45° C. under reflux conditions in 1:1 acetonitrile/tetrahydrofuran or in a 1:1:2 mixture of dichloromethane/acetonitrile/tetrahydrofuran. In a preferred embodiment the compounds of the invention are bis ketone arylene compounds having a third nitrogenous substituent. The nitrogenous substituent can be further substituted with an aromatic nitrogen-containing heterocyclic compound.

More precisely the compounds of the invention are formed according to the formula:

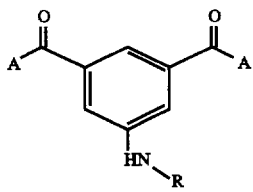

wherein A=$CH_3$ or $CH_2CH_3$ and

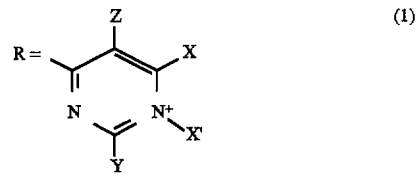

wherein X=$NH_2$, $CH_3$ or $CH_2CH_3$; X'=$CH_3$ or $CH_2CH_3$; Y=$NH_2$, $NHCH_3$, $N(CH_3)_2$; and Z=H, $CH_2$ or $CH_2CH_3$; or

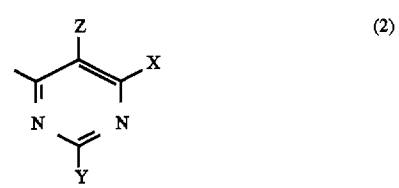

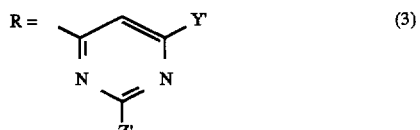

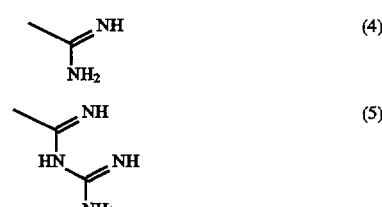

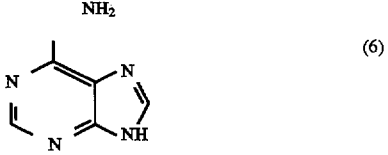

wherein Y' and Z', independently, =H, $NH_2$, $NHCH_3$, $N(CH_3)_2$ or $N^+$ $(CH_3)_3$; and salts thereof.

5.2 The Inhibition of HIV-1 Importation into the Nucleus of Non-Dividing Cells A quantitative measurement of the activity of the compounds of the invention to block the replication of HIV-1 in non-dividing cells can be determined by culture of a macrophage-tropic strain of HIV-1 on peripheral blood-derived macrophages. The cells are cultured for 5–6 days prior to infection in a medium consisting of DMEM supplemented with 10% type A/B human serum and 200 U/ml Macrophage Colony Stimulating Factor, with half the medium changed after 3 days, to reach a density of about $10^6$ cells per 5 ml well. A macrophage-tropic viral stock may be grown on these cells. The concentration of infectious particles in the stock is estimated by measurement of p24 antigen concentration.

To test the effect of compounds of the invention on HIV-1 infection in the above-described culture system, the medium is removed and replaced with medium containing HIV-1 at a concentration of 1 ng of p24 ($10^4$ $TCID_{50}$/ml (TCID=tissue culture infectious doses)) and a known concentration of the compound of the invention (the inhibitor). After 24 hours, the cultures are washed to remove non-adherent virus and the culture is re-fed with medium containing the inhibitor at the desired concentration. The amount of replication of HIV-1 is estimated by an assay of the reverse transcriptase activity or by an assay of the concentration of p24 antigen in the culture medium every 2–3 days throughout the post-infection period. In a preferred embodiment the anti-HIV potency of the candidate drug is measured by comparison of the concentration of reverse transcriptase (RT) or of p24 antigen in the medium of the treated and control cultures at the time of the peak of these values in non-treated control cultures, that is about day 5 or 6 post-infection. Repetition at various levels of inhibitor allows for the calculation of the concentration of inhibitor that achieves 50% inhibition of viral growth, $IC_{50}$. Table I discloses the $IC_{50}$ of various inhibitors.

TABLE I

| Compound | $IC_{50}$ |
| --- | --- |
| 2-amino-4-(3,5-diacetylphenyl)amino-1,6-dimethylpyrimidinium iodide (Compound No. 2) | 1 nM |
| 2-amino-4-(3-acetylphenyl)amino-1,6-dimethylpyrimidinium iodide (Compound No. 14) | 10 nM |
| 2-amino-4-(3,5-diacetylphenyl)amino-6-methylpyrimidine (Compound No. 11) | 50 nM |
| 4-(3-acetylphenyl)amino-2-amino-6-methylpyrimidine (Compound No. 15) | 15 nM |

Alternatively, the compounds may all be compared for inhibition of HIV replication at a fixed concentration. Presented in Table II are compounds that were used at a concentration of 100 nM to inhibit the production of HIV-1 in cultured monocytes infected with HIV-1 10 days prior to assay (10 ng of p24/$10^6$ cells). The production of HIV-1 in each treated culture is reported as percentage of untreated control.

TABLE II

| Compound | Viral Production |
| --- | --- |
| N-(3,5-diacetylphenyl)biguanide hydrochloride (Compound No. 12) | 12% |
| 2-(3,5-diacetylphenyl)amino-4,6-diamino-1,3,5-triazine (Compound No. 13) | 14% |
| 4-(3-acetylphenyl)amino-2-amino-6-methylpyrimidine (Compound No. 17) | 20% |
| 3,5-diacetylaniline | 20% |
| N,N-dimethyl-3,5-diacetylaniline | 25% |
| 2,6-diacetylaniline | 28% |
| 3,5-diacetylpyridine | 58% |

FIG. 2A presents further results of the use of the most active of the compounds of Table I, Compound No. 2, to block the replication of HIV-1 in purified monocytes, cultured in medium supplemented with monocyte-colony stimulating factor (M-CSF). The cultures were treated with none or between $10^{-12}$ and $10^{-6}$ M Compound No. 2 and, simultaneously with the beginning of treatment, the cells were exposed to the monocyte-tropic strain HIV-1$_{ADA}$ at about 0.01 TCID$_{50}$/cell (1 ng p24/$10^6$ cells) for 2 hours. Samples were withdrawn at days 3, 6, 10, 14 and 17 after infection and assayed for reverse transcription activity. Compound No. 2 does not inhibit reverse transcriptase, data not shown. The results show that under these conditions the $IC_{50}$ concentrations is between 0.1 and 1.0 nM and that a concentration of between 0.1 μM and 1.0 μM completely inhibits the replication of the virus.

FIGS. 2B and 2C show the effects of various concentrations of Compound No. 2 on the production of HIV-1 in monocyte cultures not supplemented with M-CSF. In these studies MOI, as determined by concentration of p24 antigen was; FIG. 2B (8 ng/$10^6$ cells) and FIG. 2C (0.8 ng/$10^6$ cells).

These experiments showed $IC_{50}$s of about 10 nM and of less than 1.0 nM respectively.

The inhibition of the replication of HIV-1 is not due to general cytotoxic effects of the compound. Concentrations of Compound No. 2 as high as 10 μM were without toxic effects on the monocyte cultures as determined by lactate dehydrogenase release and trypan blue exclusion. Further evidence of the specificity of the inhibition due to Compound No. 2 is provided by the data presented in FIGS. 3A and 3B wherein mitogen-stimulated peripheral blood leukocytes were cultured in IL-2-supplemented medium and were exposed to the HIV-1$_{ADA}$ at p24 concentrations of 10 and 1 ng/$10^6$ cells, respectively. In this experiment up to 10 μM Compound No. 2 had only a marginal effect on viral production at the higher MOI. At the lower MOI, 1 and 10 μM of Compound No. 2 caused an approximate 2-fold reduction in vital output.

The inhibition of HIV-1 importation into the nucleus of non-dividing cells can also be directly measured. One suitable method to determine directly the activity of compounds of the invention utilizes a cell line that is susceptible to HIV-1 infection, e.g., MT-4 cells, that is growth arrested by treatment with aphidicolin and exposed to HIV-1. PCR amplification is used to detect double-stranded closed circular HIV-1 genomes, which are formed only after nuclear importation, by selecting primers that bridge the junction point of the genome. For greater detail see Bukrinsky, M. I., et al., 1992, Proc. Natl. Acad. Sci. 89:6580–84.

5.3 The Treatment of HIV Infection

The present invention provides a method of treatment of HIV-1 infection by administering to an HIV-1-infected subject a pharmaceutical composition having, as an active ingredient, an effective amount of a compound of the invention. In one embodiment the compound to be administered is Compound No. 2. Pharmaceutical compositions suitable for oral, intraperitoneal, and intravenous administration can be used in the practice of the invention. Such pharmaceutical compositions include, by way of non-limiting examples, aqueous solutions of the chloride, bicarbonate, phosphate and acetate salts of Compound No. 2 and pH-buffered mixtures thereof.

The effective dose of the active ingredient can be determined by methods well known to those skilled in medicinal chemistry and pharmacology. An effective dose is the dose that achieves in the subject's plasma a concentration of the active ingredient that is sufficient to inhibit the replication of HIV-1 in monocyte cultures as described in Section 5.4, supra, but does not lead to cytopathic effects in such cultures.

The daily dose and dosing schedule to be given a subject can be determined by those skilled in the art, using the pharmacokinetic constants set forth in Table III below, to achieve a target plasma concentration. The target plasma concentration can be selected by routine pharmacological and clinical investigation methods well-known to those skilled in the art, and can be based on a range of concentrations which encompass the $IC_{50}$ calculated for each particular compound. For example, the dose can be adjusted to achieve a range of target plasma concentrations that included the $IC_{50}$ for the compounds as shown in Table I above.

TABLE III

Pharmacokinetic constants

| Compound | | | No. 2 | No. 11 | No. 15 |
|---|---|---|---|---|---|
| Area under the plasma curve | AUC | μg*hr/ml | 16.84 | 3.93 | 0.817 |
| Distribution rate constant | α | hr$^{-1}$ | 1.1193 | 1.8286 | 2.14 |
| Elimination rate constant | β | hr$^{-1}$ | 0.0046 | 0.1865 | 0.0398 |
| Initial distribution plasma level | A | μg/ml | 13.996 | 5.22 | 1.10 |
| Initial elimination plasma level | B | μg/ml | 0.054 | 0.14 | 0.0082 |
| Distribution phase half-life | $t_{1/2}\alpha$ | hr | 0.62 | 0.38 | 0.32 |
| Elimination phase half-life | $t_{1/2}\beta$ | hr | 150.46 | 3.72 | 17.41 |
| Volume of distribution | $V_\beta$ | liters | 18.33 | 7.07 | 48.29 |
| Total clearance rate | $Cl_s$ | ml/min | 1.4 | 22 | 32 |

For example, using the foregoing pharmacokinetic constants, particularly, the clearance rate, the daily dose and dosing scheule needed to obtain a given target average plasma concentration can be calculated. The results of such calculations for Compound Nos. 2, 11 and 15 are presented in Table IV. The calculated doses of Compound Nos. 2 and 15 are considerably below the toxic levels, as measured by the $LD_{50}$, of these compounds. See, Section 6.4 below.

TABLE IV

| Compound No. | M.W. | Target serum conc. | Clearance‡ (ml/min) | Dose (mg/Kg day) |
|---|---|---|---|---|
| 2* | 334 | 10 nM | 1.4 | 0.266 |
| 11 | 280 | 50 nM | 22 | 17.5 |
| 15 | 250 | 15 nM | 32 | 6.7 |

‡measured in a 25 gr mouse
*Chloride salt

Using such methods, a dose can be calculated to achieve a predetermined target plasma concentration. A practicable target plasma concentration of Compound No. 2 ranges from 0.5 nM to 10 nM; for Compound No. 11, a practicable target range is from 25 nM to 100 nM; for Compound No. 15, a practicable target range is from 7.5 nM to 50 nM.

Subjects who can benefit from the administration of the compounds of the invention according to this method include all persons infected by HIV-1. More particularly, firstly, those who benefit include those subjects who have or are at risk to develop CNS signs of HIV-1 infection and/or subjects that have developed significant weight loss. Secondly, those who benefit include those who have been recently exposed to HIV-1, but who do not yet have an established chronic infection.

5.4 Pharmaceutical Formulations

Because of their pharmacological properties, the compounds of the present invention can be used especially as agents to treat patients suffering from HIV and can be used as agents to treat patients suffering from other viral infections or chronic diseases that are dependent upon nuclear localization as part of the pathogenic process. Such a compound can be administered to a patient either by itself, or in pharmaceutical compositions where it is mixed with suitable carriers or excipient (s).

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well-known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levirating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Use of the Compounds of the Invention to Derivative Proteins

The compounds of the present invention can be used to derivatize a target protein and thereby determine the presence of adjacent $N^\varepsilon$-moieties. The test reaction can be conducted in aqueous buffer at mild to moderate alkaline pH, between about 7.2 and 8.0. Specific derivatization of the target protein can be detected by any means that separates protein-bound and free derivatizing compound. The derivatizing compound optionally can be detected by radiolabeling it. In one embodiment, the compound can be synthesized using $^{14}C$-methyliodide in place of methyliodide. Alternatively, use can be made of the strong UV absorption or fluorescence of the derivatizing compounds. Compound No. 2, for example has a absorption peak of 16,000 $M^{-1}$ $cm^{-1}$ at $\lambda=298$ nm. In a preferred embodiment the target protein is derivatized by a compound of the invention, irreversibly reduced with sodium borohydride or cyanoborohydride and fragmented into peptides by trypsin or the like. The resultant peptides can be compared with the peptides obtained from an unreacted sample of the protein by analysis using any chromatographic or electrophoretic technique that resolves peptides, e.g., reverse phase High Performance Liquid Chromatography (HPLC). When the peptides are resolved by any high resolution chromatography procedure, the derivatized peptides can be readily detected by their altered elution time and the absorbance at $\lambda=298$ nm.

In a preferred embodiment the practitioner will conduct the reaction at various pH points to determine whether a positive result can be obtained at any point within the expected range. A positive result, i.e., a result that indicates the presence of adjacent $N^\varepsilon$-moieties, is one in which a large fraction of each of a limited number, i.e., between 1–4, of peptides of the target protein are derivatized and negligible amounts of other peptides are affected.

The above-described protein derivatization technique can be used to determine whether a candidate compound can be used, according to the invention to prevent productive HIV-1 infection of macrophages. A comparison of the activity of a candidate compound and that of Compound No. 2 as derivatizing agents specific for nuclear localization sequences can be made. A compound that derivatizes the same peptides to the same extent as Compound No. 2 can be used to practice the invention.

6. EXAMPLES

6.1 Synthesis of Specific Compounds

Compound No. 2, FIG. 1A: A suspension of Compound No. 11 (2-amino-4-(3,5-diacetylphenyl)amino-6-methylpyrimidine) (0.284 g), was suspended in 1:1 acetonitrile-tetrahydrofuran was treated with methyl iodide (2 mL) and heated at 40°–45° C. under a reflux condenser for 18 hr. Cooling and filtration gave 0.35 g of 2-amino-4-(3,5-diacetylphenyl)amino-1,6-dimethylpyrimidinium iodide, mp 292° C.

Compound No. 11: A suspension of 3,5-diacetylaniline (0.885 g) in water (18 mL) was treated with 2-amino-4-chloro-6-methylpyrimidine (0.718 g) and concentrated HCl (0.42 mL) and heated at 90°–100° C. for 30 min. After cooling the mixture was treated with 10 mL of aqueous 1N KOH. The mixture was stirred for 10 min and the solid was filtered out, washed with water, and dried, to give 1.332 g of tan crystals. Recrystallization from ethyl acetate-2-methoxyethanol gave 1.175 g of 2-amino-4-(3,5-diacetylphenyl)amino-6-methylpyrimidine as light buff crystals, mp 240°–241° C.

Compound No. 12. A suspension of 3,5-diacetylaniline (0.531 g) in water (8 mL) was treated with cyanoguanidine (0.285 g) and conc. HCl (0.25 mL) and heated at reflux. After 6 hr the mixture was cooled and concentrated and 0.248 g of off-white solid was filtered out and dried to give N-(3,5-diacetylphenyl)biguanide hydrochloride, mp 260°–70° C. (dec).

Compound No. 13: A suspension of 3,5-diacetylaniline (1.95 g) in water (10 mL) was treated with 2-chloro-4,6-diamino-1,3,5-triazine (1.455 g) and concentrated HCl (0.1 mL) and heated at reflux for 20 min. After cooling the hydrochloride of Compound No. 13 separated as a white powder. This was filtered out, dissolved in 60 mL of boiling aqueous 75% methanol and treated with triethylamine (1.5 mL). On cooling, off-white flakes separated. Filtration and drying gave 1.79 g of 2-(3,5-diacetylphenyl)amino-4,6-diamino-1,3,5-triazine, mp 271°–2° C.

Compound No. 14: 4-(3-acetylphenyl)amino-2-amino-6methylpyrimidine, Compound No. 15, (0.968 g) was suspended in acetone (5 mL) containing methyl iodide (2 mL) was heated at reflux for 48 hr. Filtration after cooling gave 0.657 g of 4-(3-acetylphenyl)amino-2-amino-1,6-dimethylpyrimidinium iodide as a white powder, mp 238°–40° C.

Compound No. 15: A suspension of m-aminoacetophenone (2.7 g) and 2-amino-4-chloro-6-methylpyrimidine (2.87 g) in 40 mL water was treated with 1.7 mL concentrated HCl and heated at reflux for 1 hour. Addition of 40 mL 1N KOH gave a light buff solid, which was filtered out and dried to give 3.8 g 4-(3-acetylphenyl)amino-2-amino-6-methylpyrimidine, mp 196°–98° C.

Compound No. 16: A suspension of 3,5-diacetylaniline (0.531 g) in water (10 mL) was treated with 6-chloropurine (0.464 g) and concentrated HCl (0.25 mL) and heated at reflux for 30 min. After cooling the mixture was treated with 6 mL of aqueous 1N KOH. The mixture was stirred for 10 min and the solid was filtered out, washed with water, and dried, to give 0.80 g of 6-[(3,5-diacetylphenyl)amino] purine, mp dec 340°–350° C.

Compound No. 17: A suspension of p-aminoacetophenone (1.35 g) and 2-amino-4-chloro-6-methylpyrimidine (1.435 g) in 20 mL water was treated with 0.85 mL conc HCl and heated at reflux for 1 hr. Addition of 20 mL 1N KOH gave a light buff solid, which was filtered out and dried to give 2.28 g 4-(3-acetylphenyl)amino-2-amino-6-methylpyrimidine, mp 194°–196° C. Of this, 1.21 g was treated with methyl iodide (3 mL) in dimethylformamide (15 mL) at room temperature for 42 hr. Dilution with ethyl acetate and filtration gave 1.11 g 4-(4-acetylphenyl)amino-2-amino-1,6-dimethylpyrimidinium iodide as a white powder, mp 302°–3° C.

6.2 The Use of Compound No. 2 to Inhibit HIV Replication in Primary Macrophage lines.

6.2.1. Materials and Methods

Primary human monocytes were obtained from peripheral blood by Ficoll-Hypaque centrifugation and adherence to plastic as described previously. Gartner S. P., et al., 1986, Science 233:215. Briefly, after Ficoll-Hypaque (Pharmacia) separation, PBMCs were washed 4 times with DMEM (the last wash was done at 800 rpm to remove platelets) and resuspended in monocyte culture medium [DMEM supplemented with 1 mM glutamine, 10% heat-inactivated human serum, 1% penicillin+streptomycin mixture (Sigma)] at a density of $6 \times 10^6$ cells/ml. Cells were seeded in 24-well plates (1 ml per well) and incubated for 2 h at 37° C., 5% $CO_2$. Following incubation, cells were washed 3 times with DMEM to remove non-adherent cells and incubation was continued in monocyte culture medium supplemented with 250 U/ml human M-CSF (Sigma). Cells were allowed to mature for 7 days prior to infection with the monocyte-tropic strain, HIV-$1_{ADA}$. Nuovo, G. J., et al., 1992, Diagn. Mol. Pathol. 1:98. Two hours after infection, cells were washed with medium and cultured in RPMI supplemented with 10% human serum. In experiments where PCR analysis was performed, virus was pretreated with RNAse-free DNAse (Boehinger-Mannheim) for 2 h at room temperature and then filtered though a 0.2 μm pore nitrocellulose filter prior to infection.

PBMCs were purified by Ficoll-Hypaque centrifugation and activated by 10 μ/ml PHA-P (Sigma) and 20 U/ml recombinant human IL-2 (rhIL-2) in RPMI 1640 supplemented with 10% FBS (HyClone). After 24 h incubation, cells were washed and inoculated with HIV-$1_{ADA}$ in RPMI 1640 supplemented with 10% FBS. After a 2 h adsorption, free virus was washed away and cells were cultured in RPMI 1640 supplemented with 10% FBS and 20 U/ml rhIL-2.

Virus stock and infection

Macrophage-tropic strain HIV-$1_{ADA}$ was amplified in primary human monocytes and concentrated to produce stock with $TCID_{50}$ of about $10^5$/ml. The concentration of HIV-1 was determined by immunoassay of viral p24, concentration; using a conversion factor of 1 ng/200 HIV-1 particles.

6.2.2. p24 and RT Assay

For p24 assay, sequential 1:9 dilutions of culture supernatant were prepared and analyzed by ELISA as suggested by the manufacturer (Cellular Products, Buffalo, N.Y.). For the reverse transcriptase (RT) assay, 10 μl of culture supernatant was added to 40 μl of reaction mixture (final composition was 50 mM Tris-HCl, pH 7.8; 20 mM KCl; 5 mM $MgCl_2$; 1 mM DTT; 0.1% Triton X-100; 0.2 OD/ml polyA; 0.2 OD/ml oligo(dT)$_{12-18}$; and 40 μCi/ml $^3$H-dTTP (76 Ci/mmol, DuPont) and incubated 2 hr at 37° C. 5 μl of the reaction mixture was then spotted onto the DE 81 (Whatman) paper. Paper was air dried and washed 5 times with 5% $Na_2HPO_4$, followed by rinsing with distilled water. After air drying, paper was put on a Flexi Filter plate (Packard), covered with scintillation fluid and counted in a Top Count Microplate Counter (Packard). Results are expressed as counts per minute in 1 ml of supernatant (cpm/ml).

6.2.3. Results Dividing and Quiescent Cells

The cytotoxicity of Compound No. 2 was tested in monocyte cultures by trypan blue exclusion assay or lactate dehydrogenase (LDH) release. By both assays, no cytotoxic effect was observed with concentrations of the compound up to 10 μM (data not shown). Results presented in FIG. 2 show the effect of various concentrations of Compound 2 on HIV-1 replication in monocytes. From this experiment, we estimate the $IC_{50}$ for this compound between 0.1 and 1 nM.

Similar and higher concentrations of the compound were also tested on activated PBLs. The anti-viral effect of this compound was much less expressed in these actively dividing cell populations (FIG. 3). No anti-viral effect was detected when cultures of replicating cells were infected at the multiplicity of infection used to infect monocytes.

6.2.4. AZT and Compound No. 2 in Combination

AZT is a drug that is routinely used to treat HIV-1 infected persons. However, two factors are known to diminish the effectiveness of AZT: its toxicity and the emergence of resistant mutant strains of HIV-1. The effects of both of these factors can be reduced by administering a second, synergistic HIV-1-inhibitory drug with AZT.

In view of these premises, the effects on HIV-1 replication in human monocyte cultures of the various concentrations of AZT, alone or or in combination with 100 nM Compound No. 2, were tested using the protocols of Sections 6.2.1 and 6.2.2. Drugs were added to the monocyte cultures together with HIV-1 at about $10^5$ TCID/ml. The concentration of drugs was maintained on refeeding. HIV-1 replication was assessed by assay of the supernatant for reverse transcriptase activity. The results are expressed as mean±std. der. (cpm× $10^{-3}$) in Table V.

TABLE V

Effects of Combined AZT/Compound No. 2 on HIV-1 infected Monocyte Cultures

| | day-7 | | day-11 | |
|---|---|---|---|---|
| [AZT] | (−)No. 2 | (+)No. 2 | (−)No. 2 | (+)No. 2 |
| 0 | 1.46 ± 0.43 | 0.37 ± 0.07 | 1.81 ± 0.75 | 0.72 ± 0.30 |
| 10 pM | 0.92 ± 0.21 | 0.15 ± 0.05 | 1.63 ± 0.81 | 0.18 ± 0.06 |
| 100 pM | 0.79 ± 0.14 | 0.13 ± 0.04 | 1.34 ± 0.59 | 0.15 ± 0.06 |
| 1 nM | 0.60 ± 0.28 | 0.04 ± 0.02 | 1.07 ± 0.49 | 0.09 ± 0.03 |
| 10 nM | 0.05 ± 0.02 | 0.03 ± 0.02 | 0.08 ± 0.03 | 0.07 ± 0.03 |

These results demonstrate that there is synergy between the AZT and Compound No. 2. The synergistic effects are most pronounced at the lower doses of AZT on day 11. For example, 10 pM AZT alone produces an about 20% reduction in RT activity on day-11, 100 nM Compound No. 2 alone produces about a 60% reduction. Without synergy, the combination should produce a 70% reduction (100×(1-(0.8×0.4)). Instead the observed reduction was 90%.

6.3. The Compounds of the Invention do not block the Nuclear Importation of Essential Proteins in Cells

6.3.1. Direct Demonstration of the Inhibition of HIV-1 Nuclear Importation by Compound No. 2

The effects of Compound No. 2 on the nuclear importation of HIV-1 preintegration complexes can be directly measured by detecting the presence of circularized duplex HIV-1 genomic DNA. These duplex circles can be readily detected by PCR amplification using primers which span the junction of the circularized HIV-1 genome. Bukrinsky, M. I., et al., 1992, Proc. Natl. Acad. Sci. 89:6580–84.

Briefly, the efficiency of nuclear translocation was estimated by the ratio between the 2-LTR- and pol -specific PCR products, which reflects the portion of 2-LTR circle DNA molecules as a fraction of the entire pool of intracellular HIV-1 DNA. Viral 2-LTR circle DNA is formed exclusively within the nucleus of infected cells and thus is a convenient marker of successful nuclear translocation. Bukrinsky, M. I., 1992, Procd. Natl. Acad. Sci. 89:6580-84; Bukrinsky, M. I., 1993, Nature 365:666-669.

PCR analysis of HIV-1 DNA

Total DNA was extracted from HIV-1-infected cells using the IsoQuick extraction kit (Microprobe Corp., Garden Grove, Calif.). DNA was then analyzed by PCR using primer pairs that amplify the following sequences: a fragment of HIV-1 (LTR/gag) that is the last one to be synthesized during reverse transcription and therefore represents the pool of full-length viral DNA molecules; a fragment of polymerase gene (pol); a 2-LTR junction region found only in HIV-1 2-LTR circle DNA molecules; or a fragment of the cellular a-tubulin gene. Dilutions of 8E5 cells (containing 1 integrated copy of HIV-1 DNA per genome) into CEM cells were used as standards. Amplification products were transferred to nylon membrane filters and hybridized to $^{32}$P-labeled oligonucleotides corresponding to internal sequences specific for each PCR amplification fragment, followed by exposure to Kodak XAR-5 film or a phosphor screen.

Quantitation of PCR Reactions

Bands of correct size revealed after hybridization were quantitated with a PhosphorImager (Molecular Dynamics) by measuring the total density (integrated volume) of rectangles enclosing the corresponding product band. Efficiency of nuclear translocation of HIV-1 DNA was estimated by measurement of the amount of 2-LTR circle DNA ($N_{2-LTR}$) relative to total viral DNA ($N_{tot}$) in each culture, indexed to the same ratio of appropriate control cultures. Thus, Translocation Index=$(N_{2-LTR}/N_{tot})/(C_{2-LTR}/C_{tot}) \times 100$.

Results

Primary human monocytes were infected with HIV-1$_{ADA}$ in the presence of 100 nM concentration of Compound No. 2 or without drugs (control). Half the medium was changed every 3 days, and drugs were present throughout the whole experiment. Cell samples were taken at 48 and 96 hours post infection and the Translocation Index, relative to the drug free control was determined. At both time points the Translocation index was less than 10, indicating there was greater than 90% inhibition of nuclear importation.

6.4. Pharmacokinetic and Toxicological Studies

Toxicity

Acute whole animal toxicity determinations were made for several compounds of the present invention by estimating LD$_{50}$ values according to standard protocols. Compound 2 was emulsified in 10% DMSO/peanut oil; Compound 15 was dissolved in dH$_2$O titrated with HCl. Test compounds were administered by i.p. injection to outbred Swiss Webster ND4 mice (five mice per dosage group) according to a dose-doubling protocol beginning at 2.5 mg/kg body weight (i.e. doses of 2.5, 5, 10, 20, 40, 80, 160, 320, 640 mg/kg etc.) as required to established the LD$_{50}$. Mice were observed for 3-7 days following treatment, which comprised a single bolus injection; deaths and other overt signs of toxicity were recorded. LD$_{50}$ values were calculated from the data by non-linear regression analysis using the Chou equation, (Chou, 1976, J. Theor. Biol. 39: 253-276), and are shown in the table below:

| Acute toxicity | |
|---|---|
| | LD$_{50}$ in mg/kg (mean ± s.e.m.) |
| Compound No. 2 | 587.77 ± 65.76 |
| Compound No. 15 | 49.04 ± 0.08 |

Pharmacokinetics

Some basic pharmacokinetic constants were estimated from the appearance and clearance of the compounds of the present invention in the blood of outbred Swiss Webster ND4 mice given single i.p. doses of compound, according to standard protocols well known in the art. Compound 2 was emulsified in 10% DMSO/peanut oil and administered at 50 mg/kg. Compound 11 was dissolved in water titrated with HCl and administered at 50 mg/kg. Compound 15 was dissolved in water titrated with HCl and administered at 20 mg/kg. Blood samples were taken at intervals after bolus drug delivery, and the levels of compound were determined by ion-pair, reverse-phase chromatography utilizing a CH$_3$CN gradient in 10 mM heptane sulfonate/10 mM tetramethylammonium chloride/4.2 mM H$_3$PO$_4$ (Buffer A) and a Zorbax RX-C8 column. Column eluate was monitored at 300 nm with 500 nm as a reference wavelength. The analyte was extracted and concentrated by passing a known volume of serum over a cyanopropyl solid-phase extraction column and eluting with 95% CH$_3$CN/5% H$_2$O containing 10 mM heptane sulfonate/10 mM tetramethylammonium chloride/4.2 mM H$_3$PO$_4$. Eluted samples were evaporated to dryness and redissolved in Buffer A. Approximate values for pharmacokinetic constants were calculated from the serum concentrations using the method of residuals. See, Table III of Section 5.3 above.

Oral Availability

Compound No. 2 was dissolved in dH$_2$O and given to outbred mice at a dose of 50 mg/kg by garage. Bioavailability was estimated at 18% relative to i.p. injection (above) by monitoring plasma appearance and clearance in blood samples taken at intervals after this single bolus oral treatment. Maximal plasma concentrations (C$_{max}$) occurred at about 60 min, reaching a level of about 0.41 µg/ml.

The present invention is not to be limited in scope by the specific embodiments described which were intended as single illustrations of individual aspects of the invention, and functionally equivalent methods and components were within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A compound according to the formula:

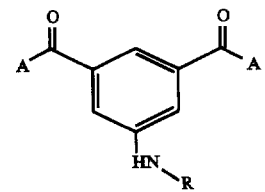

wherein A is, independently, CH$_3$ or CH$_2$CH$_3$ and R is
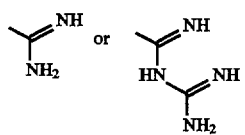
and salts thereof.
2. The compound of claim 1 wherein A=CH$_3$.
3. A pharmaceutical composition comprising a compound of claim 1 and a pharmaceutically acceptable carrier.
4. A pharmaceutical composition comprising a compound of claim 2 and a pharmaceutically acceptable carrier.
* * * * *